United States Patent
Verdier et al.

(10) Patent No.: US 11,484,052 B2
(45) Date of Patent: Nov. 1, 2022

(54) VANILLIN AND/OR ETHYLVANILLIN, PROCESS FOR THEIR PREPARATIONS AND USE THEREOF

(71) Applicant: RHODIA OPERATIONS, Paris (FR)

(72) Inventors: Stephan Verdier, Lyons (FR); Frédéric Madelaine, Cincinnati, OH (US)

(73) Assignee: RHODIA OPERATIONS, Aubervilliers (FR)

( * ) Notice: Subject to any disclaimer, the term of this patent is extended or adjusted under 35 U.S.C. 154(b) by 354 days.

(21) Appl. No.: 16/634,823

(22) PCT Filed: Jul. 26, 2018

(86) PCT No.: PCT/EP2018/070358
§ 371 (c)(1),
(2) Date: Jan. 28, 2020

(87) PCT Pub. No.: WO2019/020773
PCT Pub. Date: Jan. 31, 2019

(65) Prior Publication Data
US 2021/0120854 A1    Apr. 29, 2021

Related U.S. Application Data

(63) Continuation-in-part of application No. 15/663,312, filed on Jul. 28, 2017.

(51) Int. Cl.
*A23L 27/00* (2016.01)
*A61K 31/00* (2006.01)
*A23L 27/20* (2016.01)
*A61K 31/11* (2006.01)

(52) U.S. Cl.
CPC ............ *A23L 27/204* (2016.08); *A61K 31/11* (2013.01)

(58) Field of Classification Search
CPC .............................. A23L 27/204; A61K 31/61
See application file for complete search history.

(56) References Cited

U.S. PATENT DOCUMENTS

| | | | |
|---|---|---|---|
| 2,062,205 A | 11/1936 | Boedecker et al. | |
| 2,640,083 A * | 5/1953 | Kamlet | C07C 45/29 562/463 |
| 6,753,441 B1 | 6/2004 | Jouve et al. | |
| 8,431,750 B2 | 4/2013 | Maliverney et al. | |
| 9,284,247 B2 | 3/2016 | Garel et al. | |
| 9,567,283 B2 | 2/2017 | Garel et al. | |
| 2016/0251291 A1 | 9/2016 | Garel et al. | |
| 2017/0172184 A1 | 6/2017 | Goldsmith et al. | |
| 2019/0031588 A1 | 1/2019 | Verdier et al. | |

FOREIGN PATENT DOCUMENTS

| | | |
|---|---|---|
| JP | 49024928 | 5/1974 |
| WO | 2007094013 A1 | 8/2007 |
| WO | 2014168473 A1 | 10/2014 |
| WO | 2015066722 A1 | 5/2015 |

OTHER PUBLICATIONS

Allard, State of Art in 11C Labelled Radiotracers Synthesis, Current Medicinal Chemistry, 2008, 15, 235-277.
Bengt, Leopold et al., "Studies on Lignin III. Oxidation of Wood from *Picea abies* (L.) *karst.* (Norway Spruce) with Nitrobenzene and Alkali", Acta Chemica Scandinavica, vol. 6, Jan. 1, 1952, pp. 38-48.
Russell D. Barrows, et al., "Analysis of chemical intermediates from low-temperature steam gasification of biomass", Fuel, IPC Science and Technology Press, Guildford, GB, vol. 63, No. 1, Jan. 1, 1984, pp. 4-8.
Durak, Halil et al., "Structural analysis of bio-oils from subcritical and supercritical hydrothermal liquefaction of *Datura stramonium* L", The Journal of Supercritical Fluids, vol. 108, Oct. 27, 2015, pp. 123-135.
Shangxian, Xie et al., "Advanced chemical design for efficient lignin bioconversion", ACS Sustainable Chemistry & Engineering, vol. 5, No. 3, Jan. 31, 2017, pp. 2215-2223.

* cited by examiner

*Primary Examiner* — Sikarl A Witherspoon
(74) *Attorney, Agent, or Firm* — Osha Bergman Watanabe & Burton LLP

(57) ABSTRACT

The present invention relates to a new bio-sourced vanillin and/or ethylvanillin, containing specific impurities. The invention further relates to a process for their preparations and the use of such compounds.

24 Claims, No Drawings

VANILLIN AND/OR ETHYLVANILLIN, PROCESS FOR THEIR PREPARATIONS AND USE THEREOF

CROSS-REFERENCE TO RELATED APPLICATIONS

The present application is a U.S. national stage entry under 35 U.S.C. § 371 of International Application No. PCT/EP2018/070358, filed Jul. 28, 2018, which claims priority to U.S. patent application Ser. No. 15/663,312 filed Jul. 28, 2017, the entire content of these applications being incorporated herein by reference for all purposes.

TECHNICAL FIELD

The present invention relates to a new vanillin and/or ethylvanillin, a process for their preparations and the use of such compounds.

BACKGROUND

Vanillin, whose chemical name is 4-hydroxy-3-methoxybenzaldehyde, is one of the most important aromatic flavor compound used in food, beverages, fragrances and pharmaceuticals. Vanillin was historically extracted from *Vanilla planifolia, Vanilla tahitiensis* and *Vanilla pompona* pods. Today, as a result of constantly rising demand, less than 5% of worldwide vanillin production comes from *vanilla* orchid. Currently, chemical synthesis is the most important process for producing vanillin.

Synthetic flavourings tend to be less well liked by consumers than flavourings of natural origin. There is thus a growing interest in other sources of vanillin and in particular routes using natural raw material that can be labelled either natural or bio-sourced according to existing legislations.

Currently, the processes based on the bioconversion of a natural substrate by means of microorganism have attracted much attention. Advantageously, the products of such bioconversions are considered as 'natural products' by the European Community Legislation. A recent review (Kaur B, Chakraborty D. "Biotechnological and molecular approaches for vanillin production: a review" *Appl Biochem Biotechnol.* 2013 February; 169(4):1353-72) lists several biosynthetic pathways and appropriate microorganisms used for biosynthesis of vanilloids. Patent application WO 2015/066722 describes the conversion of eugenol to vanillin via microbial fermentation.

Several other documents (Leopold B. *Acta Chemica Scandinavia* 6 (1952) 38-48, Barrows et al. *Fuel* 63, 1984, 4-8, Durak et al. *J of Supercritical Fluids* 108 (2016), 123-135 or Xie et al. *ACS Sustainable Chem. Eng.* 2015, 5, 2215-223) describe the conversion of biomass or lignin leading to the preparation of various products including vanillin.

However, the productivity of most bioconversions and fermentations is often limited. It is still desirable to provide easy and economically viable process for producing vanillin from natural raw materials.

BRIEF DESCRIPTION OF THE INVENTION

In a first aspect, the invention relates to vanillin and/or ethylvanillin, which bio-based carbon content is between 75% and 100%, and comprising at least one compound selected from the group consisting of 2-hydroxy-2-(4-hydroxy-3-methoxyphenyl)acetic acid, 4-hydroxy-5-methoxy-isophthalaldehyde, 2,2'-(4-hydroxy-5-methoxy-1,3-phenylene)bis(2-hydroxyacetic acid), 2-hydroxy-3-methoxybenzaldehyde, 2-hydroxy-2-(2-hydroxy-3-methoxyphenyl)acetic acid, 2-(3-ethoxy-4-hydroxyphenyl)-2-hydroxyacetic acid, 2-(3-ethoxy-2-hydroxyphenyl)-2-hydroxyacetic acid, 2,2'-(5-ethoxy-4-hydroxy-1,3-phenylene)bis(2-hydroxyacetic acid), 5-ethoxy-4-hydroxyisophthalaldehyde, 3-ethoxy-2-hydroxybenzaldehyde, (E or Z)-3-(4-hydroxy-3-methoxybenzylidene)-7-methoxybenzofuran-2(3H)-one, (E or Z)-7-ethoxy-3-(3-ethoxy-4-hydroxybenzylidene)benzofuran-2(3H)-one, 4-hydroxy-3-methylbenzaldehyde and 4-hydroxy-3,5-dimethylbenzaldehyde.

In another aspect the invention relates to a vanillin, which bio-based carbon content is between 75% and 100%, and comprising at least one compound selected from the group consisting of 2-hydroxy-2-(4-hydroxy-3-methoxyphenyl) acetic acid, 4-hydroxy-5-methoxyisophthalaldehyde, 2,2'-(4-hydroxy-5-methoxy-1,3-phenylene)bis(2-hydroxyacetic acid), 2-hydroxy-3-methoxybenzaldehyde, 2-hydroxy-2-(2-hydroxy-3-methoxyphenyl)acetic acid, (E or Z)-3-(4-hydroxy-3-methoxybenzylidene)-7-methoxybenzofuran-2 (3H), 4-hydroxy-3-methylbenzaldehyde and 4-hydroxy-3,5-dimethylbenzaldehyde.

In another aspect, the present invention relates to an ethylvanillin, which bio-based carbon content is between 75% and 100%, and comprising at least one compound selected from the group consisting of 2-(3-ethoxy-4-hydroxyphenyl)-2-hydroxyacetic acid, 2-(3-ethoxy-2-hydroxyphenyl)-2-hydroxyacetic acid, 2,2'-(5-ethoxy-4-hydroxy-1,3-phenylene)bis(2-hydroxyacetic acid), 5-ethoxy-4-hydroxyisophthalaldehyde, 3-ethoxy-2-hydroxybenzaldehyde, and (E or Z)-7-ethoxy-3-(3-ethoxy-4-hydroxybenzylidene)benzo furan-2 (3H)-one.

In a further aspect, the invention relates to a process for the preparation of a vanillin and/or an ethylvanillin according to the invention comprising a step (a) of condensation of guaiacol and/or guetol which bio-based carbon content is between 75% and 100% with glyoxylic acid, and a step (b) of oxidation of the obtained condensation product.

In another aspect, the invention relates to the use of a vanillin and/or an ethylvanillin according to the invention as a flavor or fragrance.

Finally the invention also relates to a composition comprising a vanillin and/or an ethylvanillin according to the invention, preferably selected from the group consisting of food products, beverages, cosmetic formulations, pharmaceutical formulations, fragrances.

DETAILED DESCRIPTION OF THE INVENTION

Throughout the description the meaning of "comprising" includes the meaning of "consisting". Throughout the description the expression "from . . . to . . . " intends to include the limits.

In the present application, the expressions "bio-based material", "bio-sourced material" or "natural material" designate a product that is composed, in whole or in significant part, of biological products or renewable agricultural materials (including plant, animal, and marine materials) or forestry materials.

In the present invention, the expression "bio-based carbon" refers to carbon of renewable origin like agricultural, plant, animal, fungi, microorganisms, marine, or forestry materials living in a natural environment in equilibrium with the atmosphere. The bio-based carbon content is typically evaluated by the means of the carbon-14 dating (also referred to as carbon dating or radiocarbon dating). Furthermore, in the present invention, the "bio-based carbon content" refers to the molar ratio of bio-based carbon to the total carbon of the compound or the product. The bio-based carbon content can preferably be measured by a method consisting in measuring decay process of $^{14}C$ (carbon-14), in disintegrations per minute per gram carbon (or dpm/gC), through liquid scintillation counting, preferably according to the Standard Test Method ASTM D6866-16. Said American standard test ASTM D6866 is said to be equivalent to the ISO standard 16620-2. According to said standard ASTM D6866, the testing method may preferably utilize AMS (Accelerator Mass Spectrometry) along with IRMS (Isotope Ratio Mass Spectrometry) techniques to quantify the bio-based content of a given product.

The invention relates to vanillin and/or ethylvanillin, which bio-based carbon content is above 75%, preferably above 80%. The vanillin and/or ethylvanillin may have a bio-based carbon content of preferably between 85% and 100%, more preferably between 90% and 100%, more preferably between 95% and 100%, more preferably between 98% and 100%, and more preferably between 99% and 100%.

According to a preferred embodiment, the vanillin and/or ethylvanillin may display a mean isotopic $^{13}C$ deviation ($\delta^{13}C$) as measured by Isotope Ratio Mass Spectrometry versus so-called PDB reference of from −33‰ to −23‰ (i.e. $\delta^{13}C$=−28±5‰), preferably from −31‰ to −25‰ (i.e. $\delta^{13}C$=−28±3‰), more preferably from −30‰ to −26‰ (i.e. $\delta^{13}C$=−28±2‰).

In the present invention, the expression "$\delta^{13}C$" refers to the mean isotopic deviation of carbon-13. During photosynthesis, the assimilation of carbonic gas by plants occurs according to 3 principle types of metabolism: metabolism $C_3$, metabolism $C_4$ and metabolism CAM. The three photosynthetic processes from $C_3$, $C_4$ or CAM plants will generate isotopic effects, in particular the $^{13}C$ isotopic effect, which helps traceability of the botanic origins. Away from industrial activity, atmospheric carbon dioxide displays a mean isotopic deviation of about $\delta^{13}C$=−8‰ all over the world. The effect of $CO_2$ integration by the plant leads to a decrease of $^{13}C$ isotopic ratio in plants of about −20‰ for plants with a $C_3$ photosynthetic pathway. The $C_3$ photosynthetic pathway is very discriminative toward $^{13}C$, whereas $C_4$ plant discrimination toward $^{13}C$ is lower. As a result, the $^{13}C/^{12}C$ isotopic deviation is only lowered by about −3-4‰. As a consequence, $\delta^{13}C$ isotopic deviation of plants will vary depending of the photosynthetic mechanism. Plants with a photosynthetic metabolism of the $C_3$ type, such as rice and wheat, display a mean isotopic deviation $\delta^{13}C$ of about −28‰. Meanwhile, plants with a $C_4$ photosynthetic mechanism, such as maize, will display a mean isotopic deviation of about $\delta^{13}C$=−14‰. These ranges of $\delta^{13}C$ are typically measured when the plant itself is analysed. Molecules extracted from such plants may have slightly different $\delta^{13}C$. Presently vanillin from natural source has been obtained either from *vanilla* or through bio-conversion of ferulic acid. Ferulic acid can have multiple origins either from rice or from maize. (See C. Cochennec *Perfumer & Flavorist*, 2013, 38, 20-25). When vanillin is obtained through bio-conversion of ferulic acid from rice, the origin of such natural vanillin can be differentiated through mean isotopic $^{13}C$ deviation. Indeed ferulic acid from rice is obtained from a $C_3$ plant while vanillin from beans is obtained from a $C_4$ plant. Consequently, vanillin obtained from rice typically shows a $\delta^{13}C$=−35±2‰, whereas vanillin obtained from maize typically shows a $\delta^{13}C$=−19±2‰. The present invention further relates to a composition comprising, or consisting essentially of:

vanillin and/or ethylvanillin, which bio-based carbon content is between 75% and 100%; and at least one compound, which may be called impurity, selected from the group consisting of 2-hydroxy-2-(4-hydroxy-3-methoxyphenyl)acetic acid, 4-hydroxy-5-methoxyisophthalaldehyde, 2,2'(4-hydroxy-5-methoxy-1,3-phenylene)bis(2-hydroxyacetic acid), 2-hydroxy-3-methoxybenzaldehyde, 2-hydroxy-2-(2-hydroxy-3-methoxyphenyl)acetic acid, 2-(3-ethoxy-4-hydroxyphenyl)-2-hydroxyacetic acid, 2-(3-ethoxy-2-hydroxyphenyl)-2-hydroxyacetic acid, 2,2'-(5-ethoxy-4-hydroxy-1,3-phenylene)bis(2-hydroxyacetic acid), 5-ethoxy-4-hydroxyisophthalaldehyde, 3-ethoxy-2-hydroxybenzaldehyde, (E or Z)-3-(4-hydroxy-3-methoxybenzylidene)-7-methoxybenzofuran-2(3H)-one, (E or Z)-7-ethoxy-3-(3-ethoxy-4-hydroxybenzylidene)benzofuran-2(3H)-one, 4-hydroxy-3-methylbenzaldehyde and 4-hydroxy-3,5-dimethylbenzaldehyde.

According to a specific embodiment, The invention relates to vanillin and/or ethylvanillin, which bio-based carbon content is between 75% and 100%, and comprising at least one compound selected from the group consisting of 2-hydroxy-2-(4-hydroxy-3-methoxy-phenyl)acetic acid, 4-hydroxy-5-methoxyisophthalaldehyde, 2,2'-(4-hydroxy-5-methoxy-1,3-phenylene)bis(2-hydroxyacetic acid), 2-hydroxy-3-methoxybenzaldehyde, 2-hydroxy-2-(2-hydroxy-3-methoxyphenyl)acetic acid, 2-(3-ethoxy-4-hydroxyphenyl)-2-hydroxyacetic acid, 2-(3-ethoxy-2-hydroxyphenyl)-2-hydroxyacetic acid, 2,2'-(5-ethoxy-4-hydroxy-1,3-phenylene)bis(2-hydroxyacetic acid), 5-ethoxy-4-hydroxyisophthalaldehyde, 3-ethoxy-2-hydroxybenzaldehyde, (E or Z)-3-(4-hydroxy-3-methoxybenzylidene)-7-methoxybenzofuran-2(3H)-one, and (E or Z)-7-ethoxy-3-(3-ethoxy-4-hydroxybenzylidene) benzofuran-2(3H)-one.

Said vanillin and/or ethylvanillin may represent the major compound of the composition according to the present invention. Accordingly said vanillin or ethylvanillin may represent more than 50%, preferably more than 70%, more preferably more than 80% regarding the total weight of the composition. In a more preferred aspect of the present invention the said vanillin or ethylvanillin may represent more than 90%, preferably more than 95%, more preferably more than 96%, more preferably more than 99%, most preferably more than 99.5% regarding the total weight of the composition. The impurity may represent from 1 ppm to 5000 ppm, preferably from 1 ppm to 500 ppm, more preferably from 1 ppm to 50 ppm, most preferably from 1 ppm to 20 ppm, regarding the total weight of the composition.

Accordingly in a specific aspect of the present invention, the impurity may represent from 1 ppm to 100 ppm, preferably from 1 ppm to 50 ppm, and more preferably from 1 ppm to 10 ppm regarding the total weight of vanillin and/or ethylvanillin.

An object of the present invention relates to a vanillin which bio-based carbon content is between 75% and 100% and comprising at least one compound selected from the group consisting of 2-hydroxy-2-(4-hydroxy-3-methoxy-phenyl)acetic acid (A), 4-hydroxy-5-methoxyisophthalaldehyde (D), 2,2'-(4-hydroxy-5-methoxy-1,3-phenylene)bis(2-hydroxyacetic acid) (C), 2-hydroxy-3-methoxybenzaldehyde (E), 2-hydroxy-2-(2-hydroxy-3- methoxyphenyl)acetic acid (B), (E or Z)-3-(4-hydroxy-3-methoxybenzylidene)-7-methoxybenzofuran-2(3H)-one (K), 4-hydroxy-3-methylbenzaldehyde and 4-hydroxy-3,5-dimethylbenzaldehyde.

A

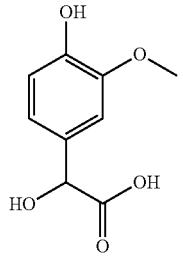

2-hydroxy-2-(4-hydroxy-3-methoxyphenyl)acetic acid

B

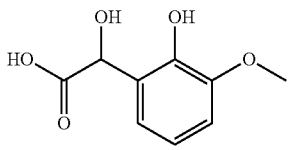

2-hydroxy-2-(2-hydroxy-3-methoxyphenyl)acetic acid

C

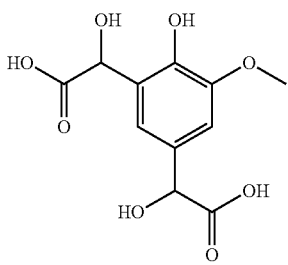

2,2'-(4-hydroxy-5-methoxy-1,3-phenylene)bis(2-hydroxyacetic acid)

D

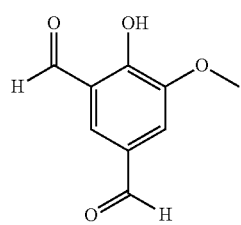

4-hydroxy-5-methoxyisophthalaldehyde

E

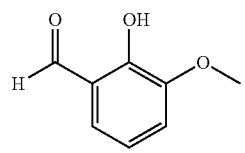

2-hydroxy-3-methoxybenzaldehyde

K

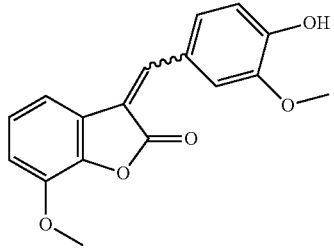

3-(4-hydroxy-3-methoxybenzylidene)-7-methoxybenzofuran-2(3H)-one

Because of its very high bio-based carbon content, the vanillin of the present invention could be similar to natural vanillin obtained from beans, or to natural vanillin obtained by bioconversion of natural sources. However, the vanillin of the present invention remains different from the other natural products because of the presence of specific impurities. The impurities contained in the vanillin of the present invention are related to the process used to prepare the vanillin. According to a specific aspect of the present invention, the vanillin of the present invention is not directly produced from lignin or biomass. In this context "directly produced from lignin or biomass" means that the vanillin may be obtained from a process of degradation of lignin or biomass. It is however not excluded that the guaiacol used in the current invention could be naturally obtained from naturally occurring substrates like lignin, pine wood or alike, by different methods. The vanillin of the present invention comprises from 1 ppm to 5000 ppm of at least one compound selected from the group consisting of 2-hydroxy-2-(4-hydroxy-3-methoxyphenyl)acetic acid (A), 4-hydroxy-5-methoxyisophthalaldehyde (D), 2,2'-(4-hydroxy-5-methoxy-1,3-phenylene)bis(2-hydroxyacetic acid) (C), 2-hydroxy-3-methoxybenzaldehyde (E), 2-hydroxy-2-(2-hydroxy-3-methoxyphenyl)acetic acid (B), (E or Z)-3-(4-hydroxy-3-methoxybenzylidene)-7-methoxybenzofuran-2(3H)-one (K), 4-hydroxy-3-methylbenzaldehyde and 4-hydroxy-3,5-dimethylbenzaldehyde.

Advantageously, the vanillin of the present invention has a purity higher than 90%, preferably higher than 95%, more preferably higher than 96%, even more preferably higher than 99%, even more preferably higher than 99.5%, most preferably higher than 99.9%.

The amount of the compounds selected from the group consisting of 2-hydroxy-2-(4-hydroxy-3-methoxyphenyl)acetic acid (A), 4-hydroxy-5-methoxyisophthalaldehyde (D), 2,2'-(4-hydroxy-5-methoxy-1,3-phenylene)bis(2-hydroxyacetic acid) (C), 2-hydroxy-3-methoxybenzaldehyde (E), 2-hydroxy-2-(2-hydroxy-3-methoxyphenyl)acetic acid (B), (E or Z)-3-(4-hydroxy-3-methoxybenzylidene)-7-methoxybenzofuran-2 (3H)-one (K), 4-hydroxy-3-methylbenzaldehyde and 4-hydroxy-3,5-dimethylbenzaldehyde may be comprised between 1 and 5000 ppm, preferably between 1 ppm and 500 ppm, more preferably between 1 ppm and 50 ppm, most preferably between 1 ppm and 20 ppm.

The vanillin of the present invention may be crystalline or amorphous. The vanillin of the present invention may be prepared in any form required, preferably in the form of flakes, beads, prills or powder.

It is well-known by the person skilled in the art that the organoleptic properties of a flavoring substance may depend from the presence and the quantity of some impurities. That is why the manufacturing method is critical for the flavor of the final compound. Advantageously, it was discovered that the vanillin of the present invention displays satisfactory organoleptic properties. It is worth mentioning that the organoleptic profile of the vanillin of the present invention is equivalent to the organoleptic profile of *vanilla* extracted from *vanilla* beans.

In another aspect, the present invention relates to an ethylvanillin which bio-based carbon content is between 75% and 100% and comprising at least one compound selected from the group consisting of 2-(3-ethoxy-4-hydroxyphenyl)-2-hydroxyacetic acid (F), 2-(3-ethoxy-2-hydroxyphenyl)-2-hydroxyacetic acid (G), 2,2'-(5-ethoxy-4-hydroxy-1,3-phenylene)bis(2-hydroxyacetic acid) (H), 5-ethoxy-4-hydroxyisophthalaldehyde (I), 3-ethoxy-2-hydroxybenzaldehyde (J), and (E or Z)-7-ethoxy-3-(3-ethoxy-4-hydroxybenzylidene)benzofuran-2(3H)-one (L).

F

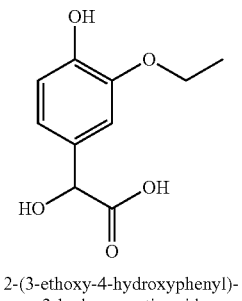

2-(3-ethoxy-4-hydroxyphenyl)-2-hydroxyacetic acid

G

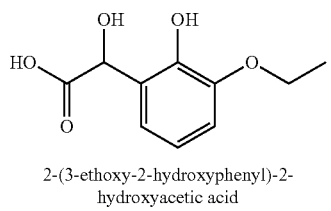

2-(3-ethoxy-2-hydroxyphenyl)-2-hydroxyacetic acid

H

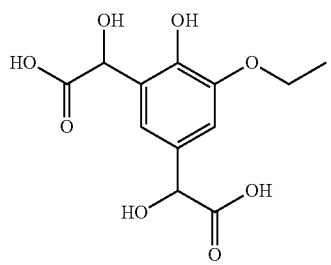

2,2'-(5-ethoxy-4-hydroxy-1,3-phenylene)bis(2-hydroxyacetic acid)

I

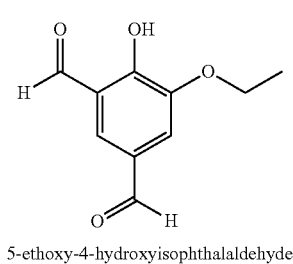

5-ethoxy-4-hydroxyisophthalaldehyde

J

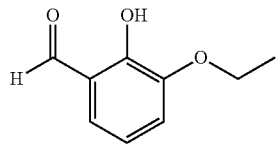

3-ethoxy-2-hydroxybenzaldehyde

L

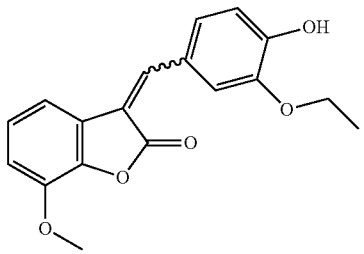

7-ethoxy-3-(3-ethoxy-4-hydroxybenzylidene)benzofuran-2(3H)-one

Advantageously, the ethylvanillin of the present invention has a purity higher than 90%, preferably higher than 95%, more preferably higher than 96%, more preferably higher than 99%, most preferably higher than 99.5%.

The amount of the compounds selected from the group consisting of 2-(3-ethoxy-4-hydroxyphenyl)-2-hydroxyacetic acid (F), 2-(3-ethoxy-2-hydroxyphenyl)-2-hydroxyacetic acid (G), 2,2'-(5-ethoxy-4-hydroxy-1,3-phenylene)bis(2-hydroxyacetic acid) (H), 5-ethoxy-4-hydroxyisophthalaldehyde (I), 3-ethoxy-2-hydroxybenzaldehyde (J), and (E or Z)-7-ethoxy-3-(3-ethoxy-4-hydroxybenzylidene)benzofuran-2(3H)-one (L) may be comprised between 1 ppm and 5000 ppm, preferably between 1 ppm and 500 ppm, more preferably between 1 ppm and 50 ppm, most preferably between 1 ppm and 20 ppm.

According to a specific aspect of the present invention, the ethylvanillin of the present invention is not directly produced from lignin or biomass.

The ethylvanillin of the present invention may be crystalline or amorphous. The ethylvanillin of the present invention may be prepared in any form required, preferably in the form of flakes, beads, prills or powder.

Advantageously, it was discovered that the ethylvanillin of the present invention displays satisfactory organoleptic properties.

Manufacturing Process

In another aspect, the present invention relates to a process for the preparation of a vanillin and/or an ethylvanillin which bio-based carbon content is between 75% and 100% comprising:

a step (a) of condensation of guaiacol and/or guetol which bio-based carbon content is between 75% and 100% with glyoxylic acid; and a step (b) of oxidation of the obtained condensation product.

In a further aspect, the present invention relates to a process for the preparation of a vanillin and/or an ethylvanillin which bio-based carbon content is between 75% and 100%, and comprising at least one compound selected from the group consisting of 2-hydroxy-2-(4-hydroxy-3-methoxyphenyl)acetic acid (A), 4-hydroxy-5-methoxyisophthalaldehyde (D), 2,2'-(4-hydroxy-5-methoxy-1,3-phenylene)bis(2-hydroxyacetic acid) (C), 2-hydroxy-3- methoxybenzaldehyde (E), 2-hydroxy-2-(2-hydroxy-3-methoxyphenyl)acetic acid (B), 2-(3-ethoxy-4-hydroxyphenyl)-2-hydroxyacetic acid (F), 2-(3-ethoxy-2-hydroxyphenyl)-2-hydroxyacetic acid (G), 2,2'-(5-ethoxy-4-hydroxy-1,3-phenylene)bis(2-hydroxyacetic acid) (H), 5-ethoxy-4-hydroxyisophthalaldehyde (I), 3-ethoxy-2-hydroxybenzaldehyde (J), (E or Z)-3-(4-hydroxy-3-methoxybenzylidene)-7-methoxybenzofuran-2(3H)-one (K), (E or Z)-7-ethoxy-3-(3-ethoxy-4-hydroxybenzylidene)benzofuran-2(3H)-one (L), 4-hydroxy-3-methylbenzaldehyde and 4-hydroxy-3,5-dimethylbenzaldehyde comprising a step (a) of condensation of guaiacol and/or guetol which bio-based carbon content is between 75% and 100% with glyoxylic acid and a step (b) of oxidation of the obtained condensation product.

Guaiacol having a bio-based carbon content above 75% is hereafter also called "bio-based guaiacol". Bio-based guaiacol according to the invention may have a bio-based carbon content above 80%, preferably between 85% and 100%, more preferably between 90% and 100%, more preferably between 95% and 100%, more preferably between 98% and 100%, and more preferably between 99% and 100%. Bio-based guaiacol is a commercial product. It could be naturally obtained from naturally occurring substrates like lignin, pine wood or alike, by different methods. In particular, different biochemical processes are available. For instance, the U.S. Pat. No. 6,235,507 discloses a microbiological process for producing vanillin and guaiacol from ferulic acid. The US patent application US 2013/0232852 discloses a method for biorefining lignin biomass.

Because of the bio-sourcing, the raw guaiacol may contain some impurities such as veratrole, 6-methyl guaiacol, alpha-cedrene or camphor. Said impurities may be specific to the origin of the compound. Typically the content of each impurity in the bio-based guaiacol may be comprised between 0.005 and 0.1%, more preferably between 0.01 and 0.08%.

Additionally guaiacol may contain other impurities such as o-cresol, m-cresol, p-cresol or 2,6-dimethylphenol.

The bio-based guaiacol used in the present invention may preferably display a mean isotopic $^{13}C$ deviation of from −33 to −23‰, more preferably from −30 to −26‰.

Guetol having a bio-based carbon content above 75% is hereafter also called "bio-based guetol". Bio-based guetol according to the invention may have a bio-based carbon content above 80%, preferably between 85% and 100%, more preferably between 90% and 100%, more preferably between 95% and 100%, more preferably between 98% and 100%, and more preferably between 99% and 100%. Bio-based guetol may be obtained from bio-based guaiacol. Processes which can be considered as natural may be used in order to transform the methyl ether function of the bio-based guaiacol into the ethyl ether function of the bio-based guetol. For example the bio-based guaiacol could be diluted in ethanol in the presence of an acid.

Because of the bio-sourcing, the raw guetol may contain some impurities such as veratrole, alpha-cedrene or camphor. Said impurities may be specific to the origin of the compound. Typically the content of each impurity in the bio-based guetol may be comprised between 1 ppm and 5000 ppm, more preferably between 5 ppm and 500 ppm.

The bio-based guetol used in the present invention displays a mean isotopic $^{13}C$ deviation of from −33 to −23‰, more preferably from −30 to −26‰.

According to a preferred embodiment of the process according to the present invention, it is possible to use only guaiacol or only guetol in the condensation step. However it is not excluded to use guaiacol and guetol simultaneously. According to another embodiment a mixture of guaiacol and guetol may be used.

Glyoxylic acid may be bio-based glyoxylic acid or non-bio-based glyoxylic acid. According to a preferred embodiment of the present invention, glyoxylic acid has a bio-based carbon content above 50% is hereafter also called "bio-based glyoxylic acid". Bio-based glyoxylic acid according to the invention may have a bio-based carbon content above 60%, preferably between 75% and 100%, more preferably between 90% and 100%, more preferably between 95% and 100%, more preferably between 98% and 100%, and more preferably between 99% and 100%. Bio-based and non-bio-based glyoxylic acid may be purchased from several producers. Some methods for producing bio-based glyoxylic acid are disclosed in the prior art. In particular, different biochemical processes are available. For instance, U.S. Pat. No. 5,219,745 discloses an industrially advantageous process for biochemical production of glyoxylic acid. Alternatively, bio-based glyoxylic acid may be produced according to well-known industrial methods (see for instance "Glyoxylic Acid" in Ullmann's Encyclopedia of Industrial Chemistry, G. MATTIODA and Y. CHRISTIDIS, Vol. 17 p. 89-92, 2012) starting from bio-based feedstock, like bio-based ethanol, bio-based glycerol or bio-based ethylene glycol.

In the condensation reaction, glyoxylic acid may be used in any form, especially in a solid form or in an aqueous solution. The glyoxylic acid may be used as an aqueous solution at a concentration ranging from, for example, between 15% and 70% by weight. Use is preferably made of commercial solutions whose concentration is about 50% by weight. According to one specific embodiment, glyoxylic acid may be monohydrate glyoxylic acid ($CHO-CO_2H$, $H_2O$). A glyoxylic acid derivative, for instance a glyoxylic acid ester such as glyoxylic acid methyl ester or glyoxylic acid ethyl ester may also be used.

Because of the bio-sourcing, the raw bio-based glyoxylic acid may contain some impurities. Said impurities may be specific to the origin of the compound.

The bio-based glyoxylic acid used in the present invention may preferably displays a mean isotopic $^{13}C$ deviation of from −33 to −7‰, preferably from −31‰ to −9‰, more preferably from −30‰ to −10‰, most preferably from −31 to −25‰.

The vanillin and/or ethylvanillin of the present invention can be prepared though any process condensing guaiacol and/or guetol and glyoxylic acid (See for example EP 0 578 550, WO 99/65853 or WO 09/077383).

The condensation reaction between guaiacol and/or guetol with glyoxylic acid allows the synthesis of the corresponding condensation product, which is a para-hydroxymandelic acid. The condensation of guaiacol and glyoxylic acid leads to 4-hydroxy-3-methoxymandelic acid (Compound A). This condensation step may give rise to some impurities, namely Compounds B and C.

The condensation of guetol and glyoxylic acid leads to 4-hydroxy-3-ethoxymandelic acid (Compound F). This condensation step may give rise to some impurities, namely Compounds G and H.

Other impurities from the guaiacol may react during the condensation step.

The mole ratio between the guaiacol and the glyoxylic acid may range between 1.0 and 4.0, preferably between 1.2 and 2.2. The mole ratio between the guetol and the glyoxylic acid may range between 1.0 and 4.0, preferably between 1.2 and 2.2.

The condensation reaction may be carried out in a cascade of stirred reactors. According to one variant, the reaction is carried out in a piston flow reactor, optionally comprising a heat exchanger. Such an embodiment is, for example, described in application WO 09/077383. The condensation reaction between guaiacol and/or guetol and glyoxylic acid can be carried out in water, in the presence of an alkali metal, said reaction being carried out in a piston flow reaction. It can also be carried out in a tubular reactor.

The condensation reaction can advantageously be catalyzed by a quaternary ammonium hydroxide, according to the reaction described in patent application EP 0 578 550.

According to an embodiment of the invention, the guaiacol and/or guetol is reacted with glyoxylic acid in the presence of a base, preferably an inorganic base or an organic base, more preferably an alkali metal, and even more preferably in the presence of NaOH or KOH. For economic reasons, sodium hydroxide may be preferred. The alkali metal hydroxide may be used in solution. In this aspect, the alkali metal hydroxide solution may have a concentration of between 10% and 50% by weight. The amount of alkali metal hydroxide introduced into the reaction medium takes into account the amount required to salify the hydroxyl function of the hydroxylated aromatic compound and the carboxylic function of glyoxylic acid. According to this variant, guaiacol is in the form of guaiacolate, respectively the guetol is in the form of guetolate and the condensation product is a mandelate compound. Generally, the amount of alkali metal hydroxide ranges between 80% and 120% of the stoichiometric amount.

Advantageously, firstly, the guaiacol and/or guetol and sodium hydroxide react to form sodium guaiacolate, respectively sodium guetolate. For example for guaiacol:

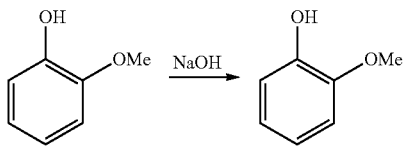

Then the guaiacolate and/or guetolate reacts with glyoxylic acid to form the corresponding para-mandelate. For example for guaiacol:

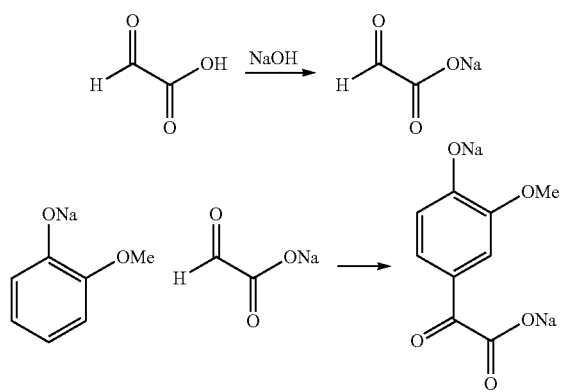

These two reaction steps for preparing the glyoxylate and the guaiacolate and/or guetolate can be carried out according to two separate steps. Alternatively, the glyoxylic acid is brought into contact directly with the guaiacolate and/or guetolate in the presence of the base.

One possible variant consists in performing the reaction in the presence of a catalyst of dicarboxylic acid type, preferably oxalic acid, as described in international patent application WO 99/65853. The amount of catalyst used, expressed by the ratio between the number of moles of catalyst and the number of moles of glyoxylic acid, may be advantageously chosen between 0.5% and 2.5% and preferably between 1% and 2%.

According to one embodiment of the present invention, guaiacol and/or guetol and the alkaline agent are mixed together before the reactive hydroxylated aromatic compound is placed in contact with the glyoxylic acid. Thus, the process according to the invention may comprise in a first stage the placing in contact of guaiacol and/or guetol with an alkali metal hydroxide in aqueous solution, followed by the placing in contact of the resulting solution with glyoxylic acid. This embodiment advantageously makes it possible to control the reaction temperature better, since the glyoxylic acid salification reaction is exothermic.

According to another embodiment, the process according to the invention comprises in a first stage the placing in contact of glyoxylic acid with an alkali metal hydroxide in aqueous solution, followed by the placing in contact of the resulting solution with guaiacol and/or guetol.

According to yet another embodiment, the process according to the invention comprises, firstly, the placing in contact of guaiacol and/or guetol with the alkaline agent in aqueous solution, and, secondly, the placing in contact of glyoxylic acid with the alkaline agent in aqueous solution, followed by the placing in contact of the two resulting solutions.

These optional steps of placing glyoxylic acid in contact with an alkali metal hydroxide in aqueous solution and/or of placing guaiacol and/or guetol in contact with the alkaline agent may be performed at a temperature of between 10° C. and 40° C., for example at 15° C. or at 35° C.

The reaction mixture obtained may have a viscosity at 20° C. of between 0.5 mPa·s and 50 mPa·s and more preferentially between 1.5 mPa·s and 3 mPa·s. According to the invention, this mixture is introduced into at least one reactor, in which the condensation reaction takes place.

According to another embodiment of the invention, the guaiacol and/or guetol is reacted with glyoxylic acid in the absence of any added acid compound or base compound. This embodiment is further disclosed in WO 2015/071431.

This condensation step may be performed in aqueous medium. In the case of a use in aqueous medium, the concentration of the guaiacol and/or guetol may preferably be between 0.5 and 1.5 mol/liter and more particularly about 1 mol/liter. Glyoxylic acid may be used in aqueous solution with a concentration ranging, for example, between 15% and 70% by weight. Use is preferably made of commercial solutions whose concentration is about 50% by weight.

According to another embodiment of the invention, the guaiacol and/or guetol is reacted with glyoxylic acid without any solvent, and the glyoxylic acid is monohydrate glyoxylic acid. This embodiment is further disclosed in WO 2015/071431.

According to another embodiment of the invention, the guaiacol and/or guetol is reacted with glyoxylic acid in the presence of a catalyst selected from the group consisting of transition metal complexes having oxygenated ligands. Said catalyst is preferentially selected from the group consisting of iron(II) acetate (Fe(OAc)$_2$), iron(III) acetate (Fe(OAc)$_3$), cupper(II) acetate (Cu(OAc)$_2$), iron(II) acetylacetonate (Fe (acac)$_2$), iron(III) acetylacetonate (Fe(acac)$_3$), cupper(II) acetylacetonate (Cu(acac)$_2$), cupper(III) acetylacetonate (Cu(acac)$_3$), and a transition metal complex having a glyoxylate ligand. This embodiment is further disclosed in WO 2015/071431.

The operating conditions of the reaction may be set as a function of the reagents and of the type of reactor or of reactor sequence used.

The reaction temperature may be between 10° C. and 90° C. According to one embodiment, the reaction temperature may be between 10° C. and 20° C. According to another embodiment, the temperature may be between 30° C. and 40° C. Furthermore, the temperature may vary during the reaction. For example, the reaction may be performed at a temperature of between 10° C. and 20° C. for a certain time, and the temperature may then be raised to between 30° C. and 50° C. for a finishing phase.

The reaction may be performed at atmospheric pressure, but under a controlled atmosphere of inert gases, preferably of nitrogen or, optionally, of rare gases, in particular argon. Nitrogen is preferentially chosen.

The total residence time of the reagents in a continuous regime and the operating or cycle time in a batch regime may vary widely, for example from a few minutes to several hours, or even several days, especially depending on the operating conditions, in particular depending on the reaction temperature. When the temperature is between 10° C. and 20° C., the total residence time of the reagents may be between 10 hours and 100 hours. When the temperature is between 30° C. and 50° C., the total residence time of the reagents may be between 30 minutes and 30 hours.

After the condensation reaction, the condensation compound obtained may be separated from the reaction mixture via standard separation techniques, especially by crystallization or by extraction using a suitable organic solvent. A neutralization step may be performed.

Alternatively, the reaction mixture obtained after the condensation reaction may be used in its existing form. However, it is preferable to recover the unreacted hydroxylated aromatic compound. Since guaiacol and/or guetol is usually in excess with respect to the glyoxylic acid, the guaiacol and/or guetol fraction which has not reacted is advantageously recovered from a recycling loop. This excess reduces the probability of forming compounds of the dimandelic acid type (i.e. compounds resulting from the condensation of two glyoxylic acid molecules with one guaiacol molecule). Unreacted guaiacol and/or guetol may be recovered by acidification, as disclosed in WO 2014/016146. It consists in adding a mineral acid, for example hydrochloric acid or sulfuric acid, to adjust the pH to between 5 and 7, and then in extracting the unreacted guaiacol and/or guetol in an organic solvent, especially in ether or toluene. After extraction, the aqueous and organic phases may be separated.

The oxidation step allows the conversion of the condensation compounds into the desired vanillin.

In addition, since the condensation product may contain impurities B and C and/or impurities G and H, which can be oxidized under the same reaction conditions, the oxidation step may produce impurities D, E and K and/or I, J and L.

Impurities obtained from guaiacol during the condensation step may be oxidized under the oxidation reaction conditions.

The oxidation may be carried out in an oxidizing atmosphere, such as O$_2$ or air.

According to one variant, the reaction medium is an alkaline aqueous medium, preferably an inorganic base and more preferably sodium or potassium hydroxide, so as to form the corresponding phenate, and to capture the released CO$_2$, in carbonate form.

The reaction may be carried out continuously or batchwise, for example in a medium strongly diluted in water.

The reaction can be catalyzed. A catalyst of this oxidation reaction may be selected from catalysts comprising at least one metal element selected from the group formed by copper, nickel, cobalt, iron, manganese, and any mixture thereof. By way of examples of inorganic or organic copper compounds, mention may in particular be made, as copper compounds, of cuprous and cupric bromide; cuprous iodide; cuprous and cupric chloride; basic cupric carbonate; cuprous and cupric nitrate; cuprous and cupric sulfate; cuprous sulfite; cuprous and cupric oxide; cupric hydroxide; cuprous and cupric acetate; and cupric trifluoromethyl sulfonate. As specific examples of nickel derivatives, mention may be made of nickel(II) halides, such as nickel(II) chloride, bromide or iodide; nickel(II) sulfate; nickel(II) carbonate; the salts of organic acids comprising from 1 to 18 carbon atoms, such as, in particular, acetate or propionate; nickel(II) complexes, such as nickel(II) acetylacetonate, nickel(II) dichlorobis(triphenylphosphine) or nickel(II) dibromobis(bipyridine); and nickel(0) complexes, such as nickel(0) bis(cycloocta-1,5-diene) or nickel(0) bisdiphenylphosphinoethane. As examples of cobalt-based compounds, mention may in particular be made of cobalt(II) and (III) halides, such as cobalt(II) chloride, bromide or iodide or cobalt(III) chloride, bromide or iodide; cobalt(II) and cobalt(III) sulfate; cobalt(II) carbonate, basic cobalt(II) carbonate; cobalt (II) orthophosphate; cobalt(II) nitrate; cobalt(II) and cobalt (III) oxide; cobalt(II) and cobalt(III) hydroxide; the salts of organic acids comprising from 1 to 18 carbon atoms, such as, in particular, cobalt(II) and cobalt(III) acetate or cobalt (II) propionate; cobalt(II) complexes, such as hexaminecobalt(II) or (III) chloride, hexaminecobalt(II) or (III) sulfate, pentaminecobalt(III) chloride or triethylenediaminecobalt (III) chloride. Use may also be made of iron-based catalytic systems, generally in the form of oxides, of hydroxides or of salts, such as iron(II) and iron(III) chloride, bromide, iodide or fluoride; iron(II) and iron(III) sulfate; iron(II) and iron (III) nitrate; or iron(II) and iron(III) oxide. The oxidation reaction can be catalyzed, for example, by a catalytic system comprising two metal elements selected from the group formed by copper, nickel, cobalt, iron, manganese, and any mixture thereof. The teachings of WO 2008/148760 may be applied for the preparation of a VA and/or EVA according to the present invention.

Firstly, the condensation compound reacts with the base (preferably sodium hydroxide) so as to salify the phenate function of the condensation compound. Then, the oxidation in an oxidizing medium (preferably in air) produces vanillate and/or ethylvanillate and CO$_2$ (trapped in carbonate form). At the end of the oxidation reaction, the precursors of vanillin and/or ethylvanillin, i.e. with a hydroxyl group in salified (ionic) form, and various impurities, including tars, are obtained. In a subsequent step, the acidification of vanillin and/or ethylvanillin in the reaction medium is carried out using a strong acid, for example sulfuric acid. The noble product, namely vanillin and/or ethylvanillin is recovered in the presence of tars. To separate vanillin and/or ethylvanillin from the crude reaction mixture, a known method consists in carrying out the extraction thereof using an organic solvent.

Advantageously, the process comprises:
the separation of vanillin and/or ethylvanillin from the reaction mixture by extraction with an organic solvent; and
the recovery and the recycling of the organic solvent used for the extraction.

According to another embodiment of the invention, the oxidation reaction may be carried out in the absence of any added acid compound or base compound. This embodiment is further disclosed in WO 2015/071431.

In another aspect of the present invention, the vanillin and/or ethylvanillin obtainable by the process as disclosed above is a subject-matter of the present invention. This compound differs from the compounds already known in the art by the fact that they are prepared from raw materials originating from natural or renewable sources.

This specificity of the vanillin and/or ethylvanillin can be determined by a bio-based carbon content measure.

The vanillin and/or ethylvanillin of the present invention may advantageously be used as a flavour or a fragrance. Preferably the vanillin and/or ethylvanillin of the present invention may be used in industry, for instance in the food, pharmaceutical or cosmetics industry, in particular for example for manufacturing fragrances.

In another aspect the present invention relates to a composition of vanillin and ethylvanillin according to the present invention. In a preferred embodiment the molar ratio of vanillin/ethylvanillin is equal to 2.

Another object of the present invention relates to a composition comprising a vanillin and/or ethylvanillin of the present invention preferably selected from the group consisting of food products, beverages, cosmetic formulations, pharmaceutical formulations and fragrances.

The disclosure of all patent applications, and publications cited herein are hereby incorporated by reference, to the extent that they provide exemplary, procedural or other details supplementary to those set forth herein. Should the disclosure of any of the patents, patent applications, and publications that are incorporated herein by reference conflict with the present specification to the extent that it might render a term unclear, the present specification shall take precedence.

Each and every claim is incorporated into the specification as an embodiment of the present invention. Thus, the claims are a further description and are an addition to the preferred embodiments of the present invention.

While preferred embodiments of this invention have been shown and described, modifications thereof can be made by one skilled in the art without departing from the spirit or teaching of this invention. The embodiments described herein are exemplary only and are not limiting. Many variations and modifications of systems and methods are possible and are within the scope of the invention.

Accordingly, the scope of protection is not limited by the description set out above, but is only limited by the claims which follow, that scope including all equivalents of the subject matter of the claims.

EXAMPLES

1. Starting Materials
Guaiacol from natural origin having a bio-based carbon content of 100%, notably containing cresol (ortho, meta and para) and 2,6-dimethylphenol.
Glyoxylic acid rom natural origin having a bio-based carbon content of 100%.
The bio-based carbon content is measured according to the Standard Test Method ASTM D6866-16.

2. Condensation
To a 2-liter 316 L glass reactor equipped with a jacket, with a mechanical stirrer, with a pH electrode, with a reflux condenser system and with an inert gas inlet are continuously charged:
600 g of demineralized water
146 g (1.1 mol) of an aqueous solution of sodium hydroxide at 30% by weight
100 g (0.8 mol) of guaiacol.
This reaction mixture is maintained at a temperature of 35° C. An aqueous solution of glyoxylic acid at 50% by weight (58 g, 0.39 mol) is then added to the reactor.
The overall residence time is 2.5 hours.
At the outlet of the reactor, a sample of this reaction medium is taken and the compounds present in the mixture are assayed by liquid chromatography.
The results obtained are as follows:
conversion of guaiacol (GA): 45%
Compounds A (87%), B (5%), and C (8%) are formed in the reaction.

3. Oxidation
A stainless steel oxidation reactor equipped with a self-suction stirrer of cavitation type ("cavitator") or of Rushton type and with a jacket for efficient cooling is continuously fed with:
the mixture of the catalyst and of the aqueous solution of mandelic compounds from the condensation reaction. i.e:
1.5 kg of reaction medium resulting from the condensation reaction. This mixture contains about 100 g of 2-hydroxy-2-(4-hydroxy-3-methoxyphenyl)acetic acid (A), 7 g of 2-hydroxy-2-(2-hydroxy-3-methoxyphenyl)acetic acid (B) and 10.6 of 2,2'-(4-hydroxy-5-methoxy-1,3-phenylene)bis(2-hydroxyacetic acid) (C).
0.8 g of an aqueous solution of $CuSO_4$ in an amount expressed as molar percentage of metal relative to the molar sum of the mandelic acids: 0.06%;
the appropriate amount of an aqueous solution of sodium hydroxide at 50% by weight corresponding at least to the amount required by the stoichiometry of the oxidation reaction;
the amount of oxygen at atmospheric pressure sufficient to have a virtually complete conversion of the mandelic acids. The oxidizing agent may be oxygen at atmospheric pressure or pressurized air.
This reaction is carried out at 75° C. At the outlet of the reactor, a sample of this reaction medium is taken and the compounds present in the mixture are assayed by liquid chromatography.
The results obtained are as follows:
conversion of 2-hydroxy-2-(4-hydroxy-3-methoxyphenyl)acetic acid: >99.5%
Yield of vanillin VA: 95%

4. Purification
The reaction mixture is then purified to obtain pure crystallised vanillin. Purity of vanillin>99% This pure vanillin is further analysed and comprises:
4-hydroxy-5-methoxyisophthalaldehyde (Compound D)<30 ppm,
(E or Z)-3-(4-hydroxy-3-methoxybenzylidene)-7-methoxybenzofuran-2(3H)-one (Compound K)<400 ppb,
4-hydroxy-3-methylbenzaldehyde: 200 ppm,
4-hydroxy-3,5-dimethylbenzaldehyde: 150 ppm.
Bio-based carbon content=100%.

The invention claimed is:

1. A composition, comprising vanillin and/or ethylvanillin, and at least one compound selected from the group consisting of 2-hydroxy-2-(4-hydroxy-3-methoxyphenyl)acetic acid, 4-hydroxy-5-methoxyisophthalaldehyde, 2,2'-(4-hydroxy-5-methoxy-1,3-phenylene)bis(2-hydroxyacetic acid), 2-hydroxy-3-methoxybenzaldehyde, 2-hydroxy-2-(2-hydroxy-3-methoxyphenyl)acetic acid, 2-(3-ethoxy-4-hydroxyphenyl)-2-hydroxyacetic acid, 2-(3-ethoxy-2-hydroxyphenyl)-2-hydroxyacetic acid, 2,2'-(5-ethoxy-4-hydroxy-1,3-phenylene)bis(2-hydroxyacetic acid), 5-ethoxy-4-hydroxyisophthalaldehyde, 3-ethoxy-2-hydroxybenzaldehyde, (E or Z)-3-(4-hydroxy-3-methoxybenzylidene)-7-methoxybenzofuran-2(3H)-one, (E or Z)-7-ethoxy-3-(3-ethoxy-4-hydroxybenzylidene)benzofuran-2(3H)-one, 4-hydroxy-3-methylbenzaldehyde, and 4-hydroxy-3,5-dimethylbenzaldehyde,
wherein the vanillin and/or ethylvanillin has a purity higher than 90% and a bio-based carbon content of between 75% and 100%, and
wherein the vanillin and/or ethylvanillin exhibits a mean isotopic $^{13}$C deviation of from 33‰ to −23‰.

2. The composition according to claim 1, wherein vanillin and/or ethylvanillin has a bio-based carbon content above 80%.

3. The composition according to claim 1 wherein the vanillin and/or ethylvanillin is not directly produced from lignin or biomass.

4. The composition according to claim 1, wherein the composition comprises vanillin and the at least one compound is selected from the group consisting of 2-hydroxy-2-(4-hydroxy-3-methoxyphenyl)acetic acid, 4-hydroxy-5-methoxyisophthalaldehyde, 2,2'-(4-hydroxy-5-methoxy-1,3-phenylene)bis(2-hydroxyacetic acid), 2-hydroxy-3-methoxybenzaldehyde, 2-hydroxy-2-(2-hydroxy-3-methoxyphenyl)acetic acid, (E or Z)-3-(4-hydroxy-3-methoxybenzylidene)-7-methoxybenzofuran-2(3H), 4-hydroxy-3-methylbenzaldehyde, and 4-hydroxy-3,5-dimethylbenzaldehyde.

5. The composition according to claim 1, wherein the composition comprises vanillin having a purity higher than 95%.

6. The composition according to claim 4, wherein the amount of the at least one compound is between 1 and 5000 ppm.

7. The composition according to claim 1, wherein the composition comprises vanillin and is in the form of flakes, beads, prills, or powder.

8. The composition according to claim 1, wherein the composition comprises vanillin and the composition exhibits satisfactory organoleptic properties.

9. The composition according to claim 1, wherein the composition comprises ethylvanillin and the at least one compound is selected from the group consisting of 2-(3-ethoxy-4-hydroxyphenyl)-2-hydroxyacetic acid, 2-(3-ethoxy-2-hydroxyphenyl)-2-hydroxyacetic acid, 2,2'-(5-ethoxy-4-hydroxy-1,3-phenylene)-bis(2-hydroxyacetic acid), 5-ethoxy-4-hydroxyisophthalaldehyde, 3-ethoxy-2-hydroxybenzaldehyde, and (E or Z)-7-ethoxy-3-(3-ethoxy-4-hydroxybenzylidene)-benzofuran-2(3H)-one.

10. The composition according to claim 1, wherein the composition comprises ethylvanillin having a purity higher than 95%.

11. The composition according to claim 9, wherein the composition comprises ethylvanillin and the amount of the at least one compound is between 1 ppm and 5000 ppm.

12. The composition according to claim 1, wherein the composition comprises ethylvanillin and is in the form of flakes, beads, prills or powder.

13. A process for the preparation of a composition that comprises vanillin and/or ethylvanillin having a bio-based carbon content of between 75% and 100% and exhibits a mean isotopic $^{13}$C deviation of from −33‰ to −23‰, comprising:
(a) condensing guaiacol and/or guetol that has a bio-based carbon content is between 75% and 100%, with glyoxylic acid to obtain a condensation product, and
(b) oxidizing the condensation product,
wherein the composition further comprises:
at least one compound selected from the group consisting of 2-hydroxy-2-(4-hydroxy-3-methoxyphenyl)acetic acid, 4-hydroxy-5-methoxyisophthalaldehyde, 2,2'-(4-hydroxy-5-methoxy-1,3-phenylene)bis(2-hydroxyacetic acid), 2-hydroxy-3-methoxybenzaldehyde, 2-hydroxy-2-(2-hydroxy-3-methoxyphenyl)acetic acid, 2-(3-ethoxy-4-hydroxyphenyl)-2-hydroxyacetic acid, 2-(3-ethoxy-2-hydroxyphenyl)-2-hydroxyacetic acid, 2,2'-(5-ethoxy-4-hydroxy-1,3-phenylene)bis(2-hydroxyacetic acid), 5-ethoxy-4-hydroxyisophthalaldehyde, 3-ethoxy-2-hydroxybenzaldehyde, (E or Z)-3-(4-hydroxy-3-methoxybenzylidene)-7-methoxybenzofuran-2(3H)-one, and (E or Z)-7-ethoxy-3-(3-ethoxy-4-hydroxybenzylidene)benzofuran-2(3H)-one, 4-hydroxy-3-methylbenzaldehyde, and 4-hydroxy-3,5-dimethylbenzaldehyde.

14. A process for the preparation of a composition comprising vanillin and/or ethylvanillin according to claim 1 comprising:
(a) condensing guaiacol having a bio-based carbon content of between 75% and 100%, and/or guetol having a bio-based carbon content of between 75% and 100%, with glyoxylic acid to obtain a condensation product, and
(b) oxidizing the condensation product.

15. A process according to claim 13, wherein glyoxylic acid has a bio-based carbon content of above 50%.

16. A process according to claim 13, wherein the mole ratio of the guaiacol and/or guetol to the glyoxylic acid is between 1.0 and 4.0.

17. A food, cosmetic or pharmaceutical composition comprising a vanillin and/or composition according to claim 1 as a flavor or fragrance.

18. A composition comprising:
vanillin and/or ethylvanillin having a bio-based carbon content of between 75% and 100% and exhibits a mean isotopic $^{13}$C deviation of from −33‰ to −23‰; and
at least one compound selected from the group consisting of 2-hydroxy-2-(4-hydroxy-3-methoxyphenyl)acetic acid, 4-hydroxy-5-methoxyisophthalaldehyde, 2,2'-(4-hydroxy-5-methoxy-1,3-phenylene)bis(2-hydroxyacetic acid), 2-hydroxy-3-methoxybenzaldehyde, 2-hydroxy-2-(2-hydroxy-3-methoxyphenyl)acetic acid, 2-(3-ethoxy-4-hydroxyphenyl)-2-hydroxyacetic acid, 2-(3-ethoxy-2-hydroxyphenyl)-2-hydroxyacetic acid, 2,2'-(5-ethoxy-4-hydroxy-1,3-phenylene)bis(2-hydroxyacetic acid), 5-ethoxy-4-hydroxyisophthalaldehyde, 3-ethoxy-2-hydroxybenzaldehyde, (E or Z)-3-(4-hydroxy-3-methoxybenzylidene)-7-methoxybenzofuran-2(3H)-one, and (E or Z)-7-ethoxy-3-(3-ethoxy-4-hydroxybenzylidene)benzofuran-2(3H)-one, 4-hydroxy-3-methylbenzaldehyde, and 4-hydroxy-3,5-dimethylbenzaldehyde.

19. A composition according to claim 18, wherein the vanillin and/or ethylvanillin is present in an amount of more than 50% of the total weight of the composition.

20. A composition according to claim 18, wherein the vanillin and/or ethylvanillin is present in an amount of more than 90% of the total weight of the composition.

21. A composition according to claim 18, wherein at least compound is present in an amount of from 1 ppm to 5000 ppm of the total weight of the composition.

22. A composition according to claim 18, wherein at least compound is present in an amount of from 1 ppm to 100 ppm based on the total weight of vanillin and/or ethylvanillin.

23. A composition according to claim 18, wherein said composition comprises vanillin and ethylvanillin and the vanillin/ethylvanillin molar ratio is equal to 2.

24. A product composition, comprising a vanillin and/or ethylvanillin composition according to claim 1, wherein the product composition is selected from the group consisting of food products, beverages, cosmetic formulations, pharmaceutical formulations, and fragrances.

* * * * *